United States Patent [19]
Carleton et al.

[11] Patent Number: 5,703,299
[45] Date of Patent: Dec. 30, 1997

[54] EXHAUST STACK SENSOR PROBE

[75] Inventors: Finis E. Carleton, San Marino; Joe W. Holtrop, Bakersfield, both of Calif.

[73] Assignee: Corona Energy Partners, Ltd., Houston, Tex.

[21] Appl. No.: 667,393

[22] Filed: Jun. 21, 1996

[51] Int. Cl.⁶ .................................................. G01N 1/00
[52] U.S. Cl. .................................................. 73/863.83
[58] Field of Search ................. 73/1 G, 863.81–863.86, 73/863.33, 863.51, 863.31, 863.83

[56] References Cited

U.S. PATENT DOCUMENTS

| | | | |
|---|---|---|---|
| 2,034,281 | 3/1936 | Bucholz | 73/27 |
| 2,906,126 | 9/1959 | Brown | 73/863.83 |
| 3,209,343 | 9/1965 | Duham et al. | 73/31.02 |
| 3,678,487 | 7/1972 | Ludewig, Jr. et al. | 340/236 |
| 3,765,842 | 10/1973 | Purt | 23/232 R |
| 3,888,123 | 6/1975 | Kuntziger et al. | 73/863.85 |
| 4,047,437 | 9/1977 | Brooks | 73/863.33 |
| 4,090,392 | 5/1978 | Smith et al. | 73/421.5 R |
| 4,346,609 | 8/1982 | Diesel | 73/863.51 |
| 4,526,028 | 7/1985 | Hubner | 73/23 |
| 4,896,526 | 1/1990 | Ratfisch | 73/1 G |
| 4,958,513 | 9/1990 | Yasunaga et al. | 73/23.2 |
| 4,981,652 | 1/1991 | Ratfisch | 422/54 |
| 5,070,738 | 12/1991 | Morgan | 73/863.83 |
| 5,293,771 | 3/1994 | Ridenour | 73/40 |
| 5,297,432 | 3/1994 | Traina et al. | 73/863.83 |

FOREIGN PATENT DOCUMENTS 996361  1/1963  United Kingdom.

OTHER PUBLICATIONS

"Evaluation Procedure For Multi-Hole Sample Probes," Yu et al, Emissions Measurement Center, 1995.

"It's not the shape, it's the holes," PSE, Inc. listing U.S. Patent 4,425,807, one page, 1994.

"Standard Flow Sensors," PSE, Inc., two pages, 1994.

"Hot Tap Flow Sensors," PSE, Inc., two pages, 1994.

"Type 75, Type 76," PSE, Inc., pp. 10, 12–15, 17, 18, 1994.

*Primary Examiner*—Robert Raevis
*Attorney, Agent, or Firm*—Guy McClung

[57] ABSTRACT

An exhaust stack stream sensor system has been invented which has a main hollow pipe with a plurality of port holes therethrough and spaced apart therealong, the main hollow pipe having two spaced apart closed off ends, the main hollow pipe positionable across the interior of an exhaust stack from which flows an exhaust stream, and a sample collecting tube having a first end in fluid communication with an interior of the main hollow pipe and a second end in fluid communication with vacuum apparatus for drawing a portion of the exhaust stream through each port hole, into the main hollow pipe, and through the sample collecting tube for transmission therefrom of a composite sample to additional apparatus.

11 Claims, 2 Drawing Sheets

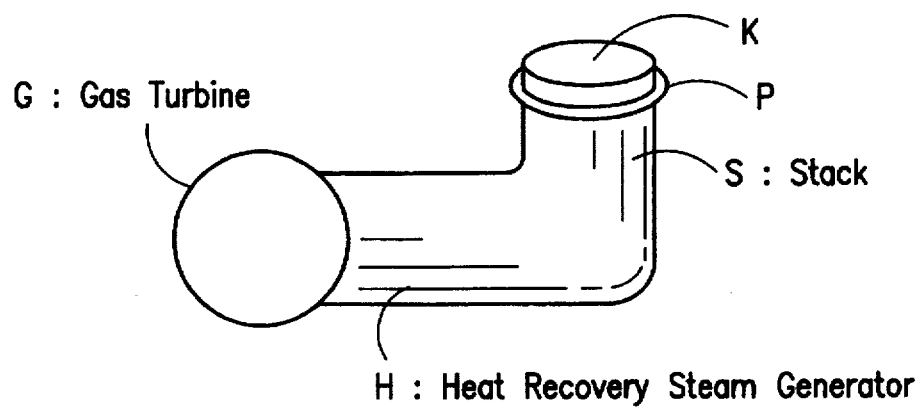
FIG. 1
PRIOR ART
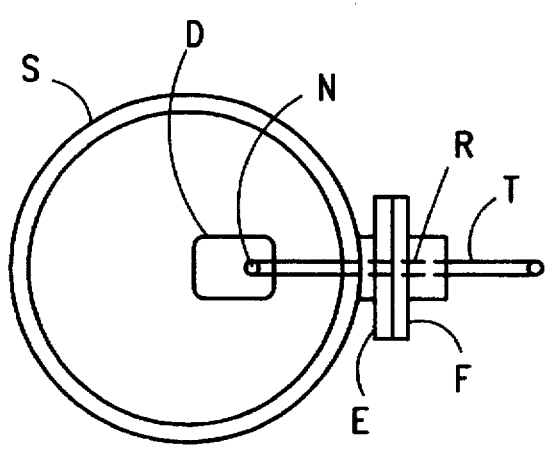 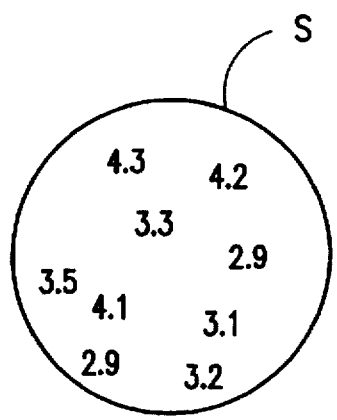
FIG. 2
PRIOR ART
FIG. 3
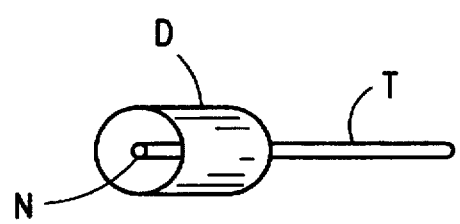
FIG. 4
PRIOR ART

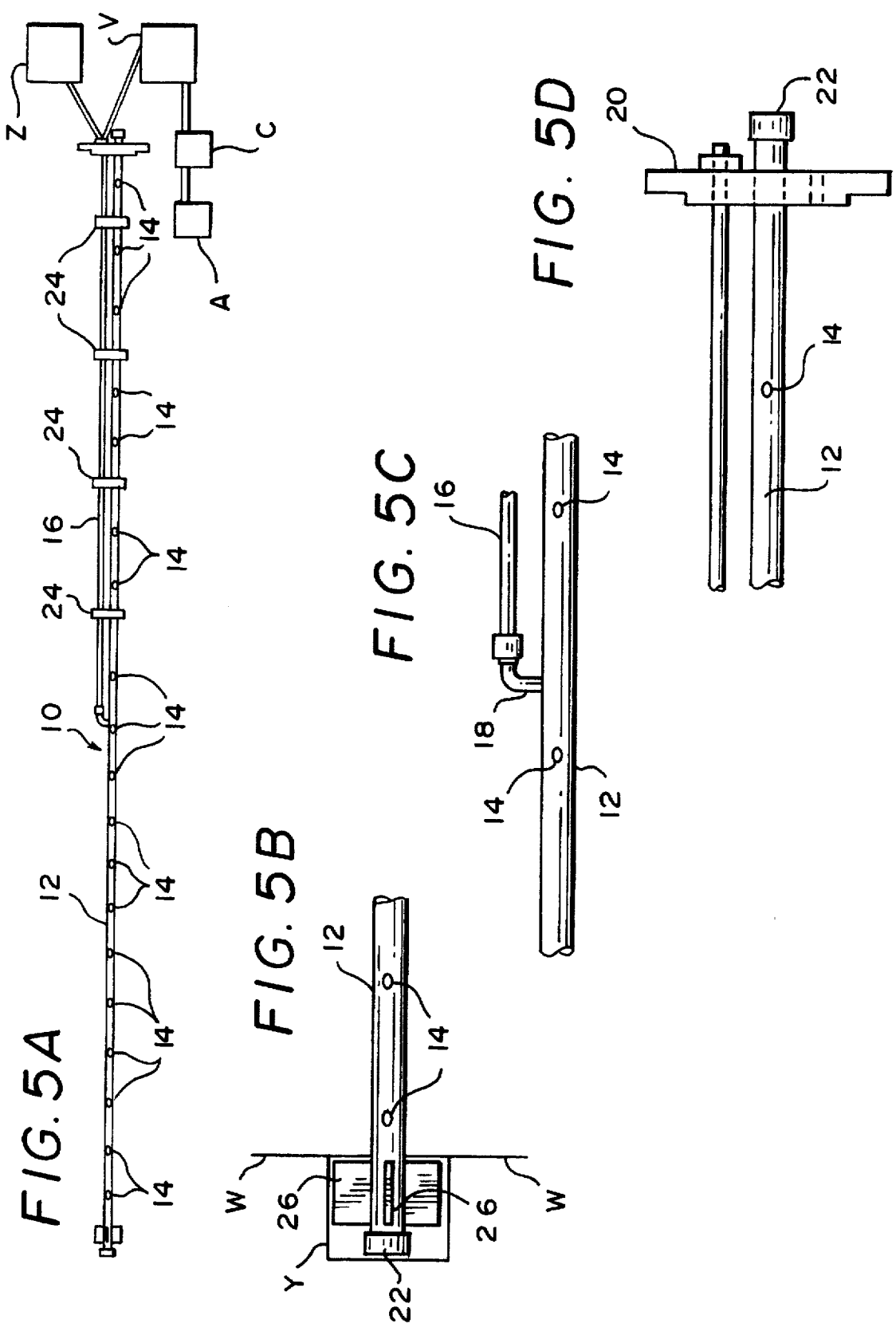

5,703,299

EXHAUST STACK SENSOR PROBE

BACKGROUND OF THE INVENTION

1. Field of the Invention

This invention is directed to the monitoring of fired machinery emissions and, in one particular aspect, to a sensing probe for monitoring contaminant concentration, e.g. (but not limited) nitrogen oxide concentration in a stream from an exhaust stack of a heat recovery steam generator for a gas turbine.

2. Description of Related Art

Certain prior art exhaust stack monitor systems for sensing contaminants, e.g. nitrogen oxides (NOX), in gas turbine exhaust have employed a single port stack probe which draws an exhaust gas sample from a single point in a stream being exhausted from a stack. The sample is then pumped to an analyzer for analysis and data recording. Typically, NOX concentration is recorded in parts per million at any give moment. This concentration level is then used to calculate pounds of NOX discharged per day through a given stack to the environment.

To insure that a single port probe produces data representative of overall stack exhaust, a government regulatory agency in California has implemented a policy on contaminant stratification for a cross-section of a stack. "Stratification" is a 10% deviation from highest to lowest contaminant concentration as determined by traversing the stack with a movable probe in a horizontal plane in two directions at right angles to each other. If stratification exists, an alternative to single point sampling is required. The purpose of the policy is to insure that the contaminant concentration value in parts per million derived from stack monitoring using a single port probe is representative of bulk contaminant discharging from an exhaust stack. The policy also seeks to insure that a single port probe is not manipulated in a non-representative manner to indicate a concentration for contaminant mass flow calculations which is lower than the overall average stack contaminant concentration.

Stratification is the uneven distribution of gaseous constituents in a duct or stack. In the California policy unacceptable stratification is the presence of a difference in excess of ten percent between the concentration of a gaseous constituent at any two points in the same cross-sectional plane.

For a particular stack exhaust it is possible that the known method for sampling an exhaust stream with a single port probe at a fixed location in an effort to obtain correct factual data regarding NOX levels will still result in inaccurate calculations. One reason for this is that an exhaust stream may not be homogeneous and may have small areas of very high NOX concentration. A fixed single port probe in the stack may sense only or primarily areas of uncommonly high or low NOX concentration—producing an inaccurate picture of the stream's real NOX level.

Blending such an exhaust stream so that it is homogeneous would require elaborate physical changes and significant capital outlay. In the prior art a movable reference probe is brought in to check the measurements of a fixed probe in a stack when stratification is present.

There has long been a need for an accurate, efficient and effective exhaust stack sampling system for sensing NOX levels. There has long been a need for such a system that produces accurate data for a non-homogeneous exhaust stream.

SUMMARY OF THE PRESENT INVENTION

In one aspect the present invention discloses a multi-port stack probe with a plurality of sampling ports through which a composite sample of an exhaust stream is drawn and transmitted to analyzing and recording systems. The probe in one aspect has a main pipe with multiple port holes and a sensing tube through which all the samples are drawn from the pipe. Since samples are drawn from a plurality of spaced apart points in the stream, the effects of areas of unrepresentative high or low NOX levels are negated. Appropriate vacuum apparatus provides the vacuum to draw samples through the ports and through the pipe.

One particular system according to the present invention utilized a multi-port probe pipe with 22 equivalently sized ports spaced apart and along opposite sides of the pipe. Samples were taken which were representative of the NOX concentration level at many points in the stream. A vacuum pump at grade level outside the stack in fluid communication with the pipe drew the samples from within the stack. In one aspect the composite sample is then transmitted to a sample conditioning system (e.g. a condenser for cooling) and then to an analyzer. Typically the sample is analyzed for NOX, carbon monoxide, and oxygen content, but it can be analyzed for any constituent or material.

The present invention discloses, in certain embodiments, an exhaust stack stream sensor system with a main hollow pipe with a plurality of port holes therethrough and spaced apart therealong, the main hollow pipe having two spaced apart closed off ends, the main hollow pipe positionable across the interior of an exhaust stack from which flows an exhaust stream, and a sample collecting tube connected to the main hollow pipe and having a first end in fluid communication with an interior of the main hollow pipe and a second end in fluid communication with vacuum apparatus for drawing a portion of the exhaust stream through each port hole, into the main hollow pipe, and through the sample collecting tube, portions of the exhaust stream thus drawn forming a composite sample of the exhaust stack stream for transmission therefrom to additional apparatus; such a system with a plurality of straps interconnecting the main hollow pipe and the sample collecting tube; such a system wherein part of the plurality of port holes are on a first side of the main hollow pipe and part of the plurality of port holes are on a second side of the hollow main pipe diametrically opposed to the first side thereof; such a system wherein the pressure drop across each hole of the plurality of port holes is at least 20 times or at least 100 times greater than pressure drop produced by fluid flowing through the main hollow pipe; such a system wherein the main hollow pipe and sample collecting tube are made of stainless steel; such a system with a back purge system in fluid communication with the sample collecting tube for clearing out the plurality of port holes; such a system with vacuum apparatus in fluid communication with the sample collecting tube for drawing fluid therethrough; such a system with conditioning apparatus in fluid communication with the vacuum apparatus for conditioning the composite sample; such a system with analysis apparatus for analyzing constituents of the composite sample; such a system wherein the main hollow pipe has one closed off end extending through a wall of the stack and movably mounted to a mount member on the outside of the stack; such a system wherein the one closed off end of the main hollow pipe has a plurality of vanes projecting therefrom which are received in and movably held in a hollow nozzle on the exterior of the stack opposite to the other end of the main hollow pipe which is mounted with a flange on the stack wall; such a system with a stack in which the exhaust stack stream sensor system is fixed, and a non-homogeneous exhaust stream flowing out through the stack; such a system wherein the holes of the plurality of port holes are sized so that an approximately similar amount of sampled fluid flows through each port hole; such a system including the stack in which the exhaust stack stream sensor system is located; and such a system wherein a non-homogeneous exhaust stream flows out through the stack, and wherein the holes of the plurality of port holes are sized so that an approximately similar amount of sampled fluid flows through each port hole. The present invention, in certain embodiments, discloses a method for obtaining a composite sample from a fluid exhaust stream of an exhaust stack, the method including drawing with vacuum apparatus a portion of the fluid exhaust stream through each of a plurality of port holes of an exhaust stack stream sensor system, the exhaust stack stream sensor system having a main hollow pipe with a plurality of port holes therethrough and spaced apart therealong, the main hollow pipe having two spaced apart closed off ends, the main hollow pipe positionable across the interior of an exhaust stack from which flows an exhaust stream, and a sample collecting tube connected to the main hollow pipe and having a first end in fluid communication with an interior of the main hollow pipe and a second end in fluid communication with vacuum apparatus for drawing a portion of the exhaust stream through each port hole, into the main hollow pipe, and through the sample collecting tube, portions of the exhaust stream thus drawn forming a composite sample of the exhaust stack stream for transmission therefrom to additional apparatus; such a method including conditioning the composite sample in conditioning apparatus; such a method including analyzing constituents of the composite sample with analysis apparatus, and recording and displaying an analysis of the constituents of the composite sample; and such a method including backpurging the exhaust stack stream sensor system to clear out the holes of the plurality of port holes.

It is, therefore, an object of at least certain preferred embodiments of the present invention to provide:

New, useful, unique, efficient, nonobvious devices and methods for sensing probe systems for sensing contaminant (e.g. but not limited to NOX) levels in exhaust stack emissions;

Such systems which account for limited areas of anomalous contaminant levels (very high or very low) in a non-homogeneous exhaust stream; and Such systems which provide accurate data about exhaust stream contaminant levels.

Certain embodiments of this invention are not limited to any particular individual feature disclosed here, but include combinations of them distinguished from the prior art in their structures and functions. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

The present invention recognizes and addresses the previously-mentioned problems and long-felt needs and provides a solution to those problems and a satisfactory meeting of those needs in its various possible embodiments and equivalents thereof. To one skilled in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

A more particular description of embodiments of the invention briefly summarized above may be had by references to the embodiments which are shown in the drawings which form a part of this specification. These drawings illustrate certain preferred embodiments and are not to be used to improperly limit the scope of the invention which may have other equally effective or legally equivalent embodiments.

FIG. 1 is a schematic view of a stack for a gas turbine exhaust which can be monitored with a system according to the present invention.

FIG. 2 is a top cross-section view of a stack with a prior art single port probe.

FIG. 3 is a schematic cross-section view of a non-homogeneous stack exhaust stream.

FIG. 4 is a perspective view of the prior art probe of FIG. 2.

FIG. 5A is a side view of a multi-port probe system according to the present invention. FIGS. 5B–5D are enlarged views of the parts of the system of FIG. 5A.

DESCRIPTION OF EMBODIMENTS PREFERRED AT THE TIME OF FILING FOR THIS PATENT

Referring now to FIG. 1, a heat recovery steam generator system H receives the exhaust from a conventional gas turbine G. The exhaust from the system H flows out from a stack S. Typically, a platform P is provided around the outside of stack S for sampling of a stack exhaust stream K.

FIG. 2 shows a prior art single port probe R for the stack S. The probe R has a sample tube T with an open end N within the stack S. The probe R is secured to the stack S with appropriate flanges E and F. A sample drawn through the end N of the tube T is conveyed to analyzing/recording apparatus (not shown). A shroud D (see FIG. 4) surrounds the end N of the tube T.

FIG. 3 is a schematic view of a stream in the stack S and the numerals indicate, for a particular illustrative exhaust stream, the location of areas of varying NOX concentration in parts per million; e.g. "4.3" means the NOX concentration at the point in the stream where the numerals 4.3 are present is 4.3 parts per million NOX. Such non-homogeneous exhaust streams are common.

FIG. 5A shows a multi-port probe system 10 according to the present invention which has a pipe 12 with multiple port holes 14 in it. Samples of the exhaust stream drawn through the holes (by a vacuum apparatus V, shown schematically in FIG. 5A) flow to a collecting tube 16 and are drawn therethrough for transmission to a sample conditioning system C (e.g. a condenser) then to analyzer/recording apparatus A.

The collecting tube 16 has an end 18 welded to the pipe 12 and in fluid communication with the interior of the pipe 12. A flange 20 provides a mounting structure for securing the system 10 within an exhaust stack. Caps 22 close off the ends of the pipe 12 and are e.g. welded on. Straps 24 secure the collecting tube 16 to the pipe 12. Vanes 26 on one end of the pipe 12 are positionable in a piece of pipe or in a hollow nozzle Y (see FIG. 5B) secured on the exterior of the stack wall W opposite the flange 20 to stabilize the pipe 12 while permitting some limited freedom of movement for the pipe end. The pipe/stack interface is sealed to prevent leakage from the stack.

In one actual embodiment the pipe 12 is a one-inch diameter hollow schedule 40 stainless steel pipe with a wall thickness of 0.133 inches and with 22 sample port holes each about 0.032 inches in diameter, with eleven holes on each side of the pipe, i.e. half the holes are diametrically opposed to, and offset from, the other half. The straps 24 in this embodiment are made of 20 gauge stainless steel and the collecting tube is made of ⅜ inch diameter stainless steel tubing. Such a system has been used successfully in an exhaust stack for an unfired heat recovery steam generator of a natural gas turbine in a 45 megawatt cogeneration plant. The turbine uses both steam injection and SCR (selective catalytic reduction) to control nitrogen oxides emissions. In this embodiment, to insure that sampling is balanced over all the port holes, the port holes have the 0.032 inch diameter mentioned earlier to give a pressure drop across each hole which is preferably significantly greater than, in this case about 100 times greater than, that of the total extracted fluid flowing through the probe itself at a sampling rate of 0.247 cubic feet/minute (but in other, embodiments hole diameter is chosen with respect to fluid flow rate so that the pressure drop is at least 20, 50, or 70 times greater than pressure drop produced by fluid flowing through the main hollow pipe). In this embodiment this system was used in a circular stack with an inside diameter of 11 feet, i.e. a stack cross-sectional area of about 95 square feet. The port holes are about six inches apart on alternating sides (not top or bottom, although this is possible) of the pipe in this embodiment. In one aspect 316 stainless steel may be used for all major system components.

In one embodiment an automatic air back purge system is connected to the collecting tube 16. The back purge system Z automatically provides back pressure air to the probe, e.g. 60 p.s.i.g. instrument quality air, e.g. for about one to ten minutes, one or more times a day to insure that the probe port holes do not become plugged by soot, particulates, entrained solids, etc.

It is within the scope of this invention to employ any pipe or conduit with a plurality of sample ports or pieces of interconnected pipe or conduit. Preferably any such system presents a smooth geometry to the fluid flow stream for minimum flow disturbance (e.g. two crossed pipes each with multiple ports may be used). Systems according to the present invention may be used with stack streams having contaminants at relatively low concentrations, e.g. below five parts per million and as low as three to four parts per million.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form it may be utilized. The invention claimed herein is new and novel in accordance with 35 U.S.C. § 102 and satisfies the conditions for patentability in § 102. The invention claimed herein is not obvious in accordance with 35 U.S.C. § 103 and satisfies the conditions for patentability in § 103. This specification and the claims that follow are in accordance with all of the requirements of 35 U.S.C. § 112.

What is claimed is:

1. An exhaust stack stream sensor system comprising a main hollow pipe with a plurality of port holes therethrough and spaced apart therealong, the main hollow pipe having two spaced apart closed off ends, the main hollow pipe positionable across the interior of an exhaust stack from which flows an exhaust stream, a sample collecting tube connected to the main hollow pipe and having a first end in fluid communication with an interior of the main hollow pipe and a second end in fluid communication with vacuum apparatus for drawing a portion of the exhaust stream through each port hole, into the main hollow pipe, and through the sample collecting tube, portions of the exhaust stream thus drawn forming a composite sample of the exhaust stack stream for transmission therefrom to additional apparatus, and a plurality of straps interconnecting the main hollow pipe and the sample collecting tube.

2. An exhaust stack stream sensor system comprising a main hollow pipe with an interior enclosed within and defined by a main pipe wall, the main hollow pipe having a plurality of port holes each extending through the main pipe wall and spaced apart therealong, each of the port holes formed and disposed so that fluid in an exhaust stream of an exhaust stack exterior to the main hollow pipe is flowable into and through the plurality of port holes directly into the interior of the main hollow pipe, the main hollow pipe having two spaced apart closed off ends, the main hollow pipe positionable across the interior of the exhaust stack from which flows the exhaust stream, vacuum apparatus, a sample collecting tube connected to the main hollow pipe and having a first end in fluid communication with the interior of the main hollow pipe and a second end in fluid communication with the vacuum apparatus, the vacuum apparatus for drawing a portion of the exhaust stream through each port hole directly into the interior of the main hollow pipe and into and through the sample collecting tube, portions of the exhaust stream thus drawn forming a composite sample of the exhaust stream for transmission therefrom to additional apparatus, and a plurality of straps interconnecting the main hollow pipe and the sample collecting tube.

3. An exhaust stack stream sensor system comprising a main hollow pipe with an interior enclosed within and defined by a main pipe wall, the main hollow pipe having a plurality of port holes each extending through the main pipe wall and spaced apart therealong, each of the port holes formed and disposed so that fluid in an exhaust stream of an exhaust stack exterior to the main hollow pipe is flowable into and through the plurality of port holes directly into the interior of the main hollow pipe, the main hollow pipe having two spaced apart closed off ends, the main hollow pipe positionable across the interior of the exhaust stack from which flows the exhaust stream, vacuum apparatus, a sample collecting tube connected to the main hollow pipe and having a first end in fluid communication with the interior of the main hollow pipe and a second end in fluid communication with the vacuum apparatus, the vacuum apparatus for drawing a portion of the exhaust stream through each port hole directly into the interior of the main hollow pipe and into and through the sample collecting tube, portions of the exhaust stream thus drawn forming a composite sample of the exhaust stream for transmission therefrom to additional apparatus, and wherein the main hollow pipe has one closed off end extending through the stack and movably mounted in a mount member outside the stack and wherein the mount member is a hollow nozzle and the one closed off end of the main hollow pipe has a plurality of vanes projecting therefrom which are received in and movably held in the hollow nozzle.

4. A method for obtaining a composite sample from an exhaust stream of an exhaust stack, the method comprising drawing with vacuum apparatus a portion of the fluid exhaust stream through each of a plurality of port holes of a main hollow pipe of an exhaust stack stream sensor system, the exhaust stack stream sensor system comprising a main hollow pipe with an interior enclosed within and defined by a main pipe wall, the main hollow pipe having a plurality of port holes each extending through the main pipe wall and spaced apart therealong, each of the port holes formed and disposed so that fluid in the exhaust stream of the exhaust stack exterior to the main hollow pipe is flowable into and through the plurality of port holes directly into the interior of the main hollow pipe, the main hollow pipe having two spaced apart closed off ends, the main hollow pipe having one closed off end extending through the stack and movably mounted in a mount member outside the stack and wherein the mount member is a hollow nozzle and the one closed off end of the main hollow pipe has a plurality of vanes projecting therefrom which are received in and movably held in the hollow nozzle, the main hollow pipe positionable across the interior of the exhaust stack from which flows the exhaust stream; vacuum apparatus; and a sample collecting tube connected to the main hollow pipe and having a first end in fluid communication with the interior of the main hollow pipe and a second end in fluid communication with the vacuum apparatus; the vacuum apparatus for drawing a portion of the exhaust stream through each port hole directly into the interior of the main hollow pipe and into and through the sample collecting tube, portions of the exhaust stream thus drawn forming a composite sample, drawing through the sample collecting tube with the vacuum apparatus the composite sample, and transmitting the composite sample from the sample collecting tube.

5. The method of claim 4 further comprising conditioning the composite sample in conditioning apparatus.

6. The method of claim 5 further comprising analyzing constituents of the composite sample with analysis apparatus, and recording and displaying an analysis of the constituents of the composite sample.

7. The method of claim 6 further comprising backpurging the exhaust stack stream sensor system to clear out the holes of the plurality of port holes.

8. A method for obtaining a composite sample from an exhaust stream of an exhaust stack, the method comprising drawing with vacuum apparatus a portion of the fluid exhaust stream through each of a plurality of port holes of a main hollow pipe of an exhaust stack stream sensor system, the exhaust stack stream sensor system comprising a main hollow pipe with an interior enclosed within and defined by a main pipe wall, the main hollow pipe having a plurality of port holes each extending through the main pipe wall and spaced apart therealong, each of the port holes formed and disposed so that fluid in the exhaust stream of the exhaust stack exterior to the main hollow pipe is flowable into and through the plurality of port holes directly into the interior of the main hollow pipe, the main hollow pipe having two spaced apart closed off ends, the main hollow pipe positionable across the interior of the exhaust stack from which flows the exhaust stream; vacuum apparatus; and a sample collecting tube connected to the main hollow pipe and having a first end in fluid communication with the interior of the main hollow pipe and a second end in fluid communication with the vacuum apparatus, a plurality of straps interconnecting the main hollow pipe and the sample collecting tube; the vacuum apparatus for drawing a portion of the exhaust stream through each port hole directly into the interior of the main hollow pipe and into and through the sample collecting tube, portions of the exhaust stream thus drawn forming a composite sample, drawing through the sample collecting tube with the vacuum apparatus the composite sample, and transmitting the composite sample from the sample collecting tube.

9. The method of claim 8 further comprising conditioning the composite sample in conditioning apparatus.

10. The method of claim 9 further comprising analyzing constituents of the composite sample with analysis apparatus, and recording and displaying an analysis of the constituents of the composite sample.

11. The method of claim 10 further comprising backpurging the exhaust stack stream sensor system to clear out the holes of the plurality of port holes.

* * * * *